(12) United States Patent
Engel et al.

(10) Patent No.: US 9,944,853 B2
(45) Date of Patent: Apr. 17, 2018

(54) COLOR INHIBITOR FOR QUATERNARY AMMONIUM HYDROXIDE IN NON-AQUEOUS SOLVENT

(71) Applicant: SACHEM, INC., Austin, TX (US)

(72) Inventors: Tim Engel, DR Tilburg Noord-brabant (NL); Alfred Van Lier, Zaltbommel (NL)

(73) Assignee: SACHEM, Inc., Austin, TX (US)

( * ) Notice: Subject to any disclaimer, the term of this patent is extended or adjusted under 35 U.S.C. 154(b) by 315 days.

(21) Appl. No.: 14/760,489

(22) PCT Filed: Jan. 10, 2014

(86) PCT No.: PCT/US2014/010955
§ 371 (c)(1),
(2) Date: Jul. 13, 2015

(87) PCT Pub. No.: WO2014/110308
PCT Pub. Date: Jul. 17, 2014

(65) Prior Publication Data
US 2015/0353824 A1    Dec. 10, 2015

Related U.S. Application Data

(60) Provisional application No. 61/751,429, filed on Jan. 11, 2013.

(51) Int. Cl.
*C09K 15/22* (2006.01)
*C07C 209/90* (2006.01)
(Continued)

(52) U.S. Cl.
CPC ............ *C09K 15/22* (2013.01); *C07C 209/90* (2013.01); *C07C 211/62* (2013.01);
(Continued)

(58) Field of Classification Search
CPC ... C07C 209/82; C07C 209/90; C07C 211/62; C07C 211/63; C07C 211/64;
(Continued)

(56) References Cited

U.S. PATENT DOCUMENTS 5,880,076 A * 3/1999 Vermeer .................. A61K 8/42
510/119
6,458,343 B1 * 10/2002 Zeman ................. A61K 8/0208
162/111
(Continued)

FOREIGN PATENT DOCUMENTS

JP         59134752        8/1984

OTHER PUBLICATIONS

PCT/US2014/010955; PCT International Search Report and Written Opinion of the International Searching Authority dated Mar. 18, 2014.
(Continued)

*Primary Examiner* — Harold Pyon
*Assistant Examiner* — Matthew R Diaz
(74) *Attorney, Agent, or Firm* — Renner, Otto, Boisselle & Sklar, LLP (57) ABSTRACT

A composition including a quaternary onium hydroxide in a non-aqueous solvent, wherein the quaternary ammonium hydroxide has a concentration in the range from about 5% by weight to about 50% by weight of the composition; and imidazolidine-2,4-dione, wherein the imidazolidine-2,4-dione has a concentration in the range from about 10 to about 5000 parts per million of the composition.

5 Claims, 5 Drawing Sheets

(51) Int. Cl.
*C07C 211/62* (2006.01)
*C07C 211/63* (2006.01)
*C07C 213/10* (2006.01)
*C07C 215/40* (2006.01)
*C07C 215/72* (2006.01)
*C07C 215/90* (2006.01)
*C07C 211/64* (2006.01)

(52) U.S. Cl.
CPC .......... *C07C 211/63* (2013.01); *C07C 211/64* (2013.01); *C07C 213/10* (2013.01); *C07C 215/40* (2013.01); *C07C 215/72* (2013.01); *C07C 215/90* (2013.01)

(58) Field of Classification Search
CPC ... C07C 213/04; C07C 213/10; C07C 215/40; C07C 215/60; C07C 215/62; C07C 215/90; C11D 1/60; C11D 1/62; C11D 3/30; C11D 3/32; C11D 3/323; C11D 3/36; C01N 25/22; C01N 25/32; C09K 15/20; C09K 15/22; C07D 247/00; C07D 247/02
USPC ....... 252/182.29; 564/2, 281, 282, 283, 284, 564/285, 286, 287, 288, 289, 290, 291, 564/292, 293, 294, 295, 296; 568/9
See application file for complete search history.

(56) References Cited

U.S. PATENT DOCUMENTS

| | | | |
|---|---|---|---|
| 7,851,653 B2 * | 12/2010 | Getman | A01N 25/34 427/384 |
| 2003/0026774 A1 | 2/2003 | Milbradt et al. | |
| 2010/0298605 A1 | 11/2010 | Hirose et al. | |
| 2014/0065836 A1 * | 3/2014 | Toben | C09K 13/02 438/745 |

OTHER PUBLICATIONS

PCT/US2014/010955; PCT International Preliminary Report on Patentability dated Jul. 23, 2015.

* cited by examiner

COLOR INHIBITOR FOR QUATERNARY AMMONIUM HYDROXIDE IN NON-AQUEOUS SOLVENT

TECHNICAL FIELD

The present invention relates to a color inhibitor for use with quaternary ammonium hydroxides in non-aqueous solvents.

BACKGROUND

Quaternary ammonium hydroxides in aqueous solution are quite stable. However, quaternary ammonium hydroxides in non-aqueous solvents tend to develop undesirable coloration on standing or storage, even at room temperature, but particularly at elevated temperatures. Although not to be bound by theory, it is considered that one reason for the color development is a Hoffman elimination of a propyl or higher length alkyl substituent of the quaternary ammonium compound, to form an alkene that subsequently reacts to form a colored compound. For example, the following reaction may take place, yielding an alkene that could polymerize or otherwise react to form a colored compound in the quaternary ammonium non-aqueous solution:

The development of color in a quaternary ammonium compound in a non-aqueous solvent is undesirable for a number of reasons, but has been a long-standing problem that has proven difficult to solve. One solution has been to add formaldehyde to the non-aqueous quaternary ammonium solution, but it is well known that formaldehyde is undesirable in many systems.

Thus, the tendency of quaternary ammonium hydroxides in non-aqueous solvents to develop undesirable coloration on standing or storage has resisted solution and there has been a long-standing need for a solution to this problem.

SUMMARY

The present invention provides a solution to the long-standing problem resulting from the tendency of quaternary ammonium hydroxides in non-aqueous solvents to develop undesirable coloration on standing or storage.

In one embodiment, the present invention includes a composition including:

a quaternary onium hydroxide in a non-aqueous solvent, wherein the quaternary onium hydroxide has a concentration in the range from about 5% by weight to about 50% by weight of the composition; and imidazolidine-2,4-dione, wherein the imidazolidine-2,4-dione has a concentration in the range from about 10 parts per million (ppm) to about 5000 ppm of the composition.

The imidazolidine-2,4-dione has a general formula (I):

and is commonly known as hydantoin.

In one embodiment, the non-aqueous solvent comprises propylene glycol (PG), butylene glycol (BG), ethylene glycol (EG), triethylene glycol (TEG), formamide (FA), and glycerol (GLY).

In one embodiment, the quaternary onium hydroxide comprises a quaternary onium ion having general formula (II):

wherein in formula (II), A is a nitrogen or phosphorus atom, $R^1$, $R^2$, $R^3$ and $R^4$ are each independently an alkyl group containing from 1 to about 20 carbon atoms, a hydroxyalkyl or an alkoxyalkyl group containing from 1 to about 20, substituted or unsubstituted aryl groups or hydroxyaryl groups containing from 6 to 18 ring carbon atoms, when substituted, said substitution comprises one or more substituent selected from any of the foregoing alkyl, hydroxyalkyl or alkoxyalkyl groups, or $R^1$ and $R^2$ or $R^3$ together with A may form a heterocyclic group provided that if the heterocyclic group contains a C=A group, $R^3$ is the second bond.

In one embodiment, the quaternary onium hydroxide in formula (II) is a quaternary ammonium hydroxide.

In one embodiment, at least one of the alkyl groups in formula (II) contains 3 or more carbon atoms.

The foregoing figures are provided by way of non-limiting examples, to demonstrate some features of the present invention.

DETAILED DESCRIPTION

As described in the background, an ongoing problem with many quaternary ammonium compounds in organic or non-aqueous solvents is the production of color in the solution due to breakdown of one or more of the alkyl chains on the quaternary ammonium molecule.

The present inventors discovered that by adding imidazolidine-2,4-dione to a solution containing a quaternary onium hydroxide in a non-aqueous solvent, i.e., in an organic solvent or other non-aqueous solvent, the undesirable discoloration can be reduced or eliminated, when the quaternary ammonium hydroxide solution is stored and/or subjected to elevated temperatures in the range from about 50° C. to about 60° C., or up to about 60° C., for periods of 10-15 days, during tests.

Thus, in one embodiment, the present invention includes a composition including:

a quaternary ammonium hydroxide in a non-aqueous solvent, wherein the quaternary ammonium hydroxide has a concentration in the range from about 5% by weight to about 50% by weight of the composition; and imidazolidine-2,4-dione, wherein the imidazolidine-2,4-dione has a concentration in the range from about 10 parts per million (ppm) to about 5000 ppm of the composition. The imidazolidine-2,4-dione has a general formula (I):

(I)

and is commonly known as hydantoin.

In one embodiment, the non-aqueous solvent comprises propylene glycol (PG), butylene glycol (BG), ethylene glycol (EG), triethylene glycol (TEG), formamide (FA), and glycerol (GLY).

In one embodiment, the quaternary onium hydroxide comprises a quaternary onium having general formula (II):

(II)

wherein in formula (II), A is a nitrogen or phosphorus atom, $R^1$, $R^2$, $R^3$ and $R^4$ are each independently a branched or unbranched alkyl group containing from 1 to about 20 carbon atoms, a branched or unbranched hydroxyalkyl or an alkoxyalkyl group containing from 1 to about 20 carbon atoms, substituted or unsubstituted aryl groups or hydroxyaryl groups containing from 6 to 18 ring carbon atoms, when substituted, said substitution comprises one or more substituent selected from any of the foregoing alkyl, hydroxyalkyl or alkoxyalkyl groups, or $R^1$ and $R^2$ or $R^3$ together with A may form a heterocyclic group provided that if the heterocyclic group contains a C=A group, $R^3$ is the second bond.

In one embodiment, the quaternary onium hydroxide in formula (II) is a quaternary ammonium hydroxide.

In one embodiment, at least one of the alkyl groups in formula (II) contains 3 or more carbon atoms.

Specific examples of ammonium hydroxides representative of Formula II wherein A=N include tetramethylammonium hydroxide, dimethyldipropylammonium hydroxide, tetrapropylammonium hydroxide, tetrabutylammonium hydroxide, tetra-n-octylammonium hydroxide, trimethylhydroxyethylammonium hydroxide, trimethylmethoxyethylammonium hydroxide, dimethyldihydroxyethylammonium hydroxide, methyltrihydroxyethylammonium hydroxide, phenyltrimethylammonium hydroxide, phenyltriethylammonium hydroxide, benzyltrimethylammonium hydroxide, benzyltriethylammonium hydroxide, methyltributylammonium hydroxide and cetyltrimethylammonium hydroxide.

Specific examples of quaternary phosphonium hydroxides representative of Formula II wherein A=P include tetramethylphosphonium hydroxide, dimethyldipropylphosphonium hydroxide, tetraethylphosphonium hydroxide, tetrapropylphosphonium hydroxide, tetrabutylphosphonium hydroxide, trimethylhydroxyethylphosphonium hydroxide, dimethyidihydroxyethylphosphonium hydroxide, methyltrihydroxyethylphosphonium hydroxide, phenyltrimethylphosphonium hydroxide, phenyltriethylphosphonium hydroxide and benzyltrimethylphosphonium hydroxide.

EXAMPLES

In the following examples, the difference between color change and color increase is that the color change is actual color measurement of the sample, the color increase is the amount of increase compared to the initial intake (thus, the measured color at the specified time minus the measured color before the sample was subjected to increased temperature/time).

Example 1

A 20% by weight solution of dimethyldipropylammonium hydroxide (DMDPA*OH) in propylene glycol is prepared. The solution contains water at less than about 0.5% by weight by Karl Fischer titration. Eleven aliquots of the solution are taken, and 1000 ppm of each of ten potential color inhibitor additives are added to one of each of the ten aliquots, and nothing is added to the eleventh aliquot ("Referentie"). Each of the eleven aliquots is divided in half, the first half of each aliquot is held at room temperature for 18 hours, and the second half of each aliquot is held at 50° C. for 36 hours. The Gardner color is determined for each aliquot at zero time, at 18 hours and again at 36 hours for the 50° C. samples. The results are shown in FIG. 1 and FIG. 2.

Figure 1:
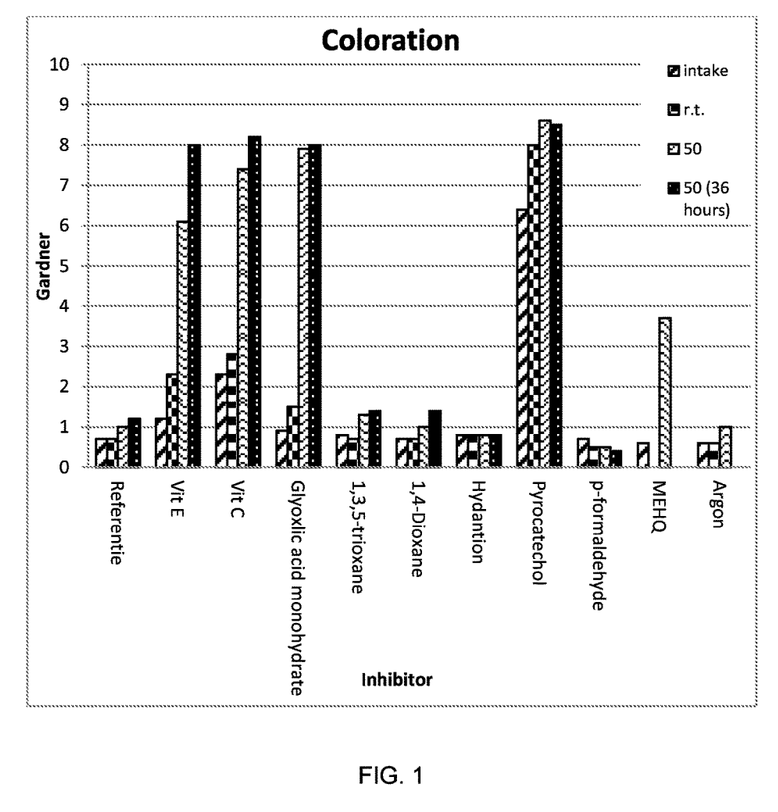
FIG. 1 is a bar graph showing the coloration (color change) in solutions of a quaternary ammonium hydroxide in a non-aqueous solvent with various candidate inhibitors added and with no inhibitor added.

FIG. 1 is a bar graph showing the coloration (color change) in solutions of the DMDPA*OH in the non-aqueous solvent propylene glycol with various candidate inhibitors added and with no inhibitor added, according to Example 1.

Figure 2:
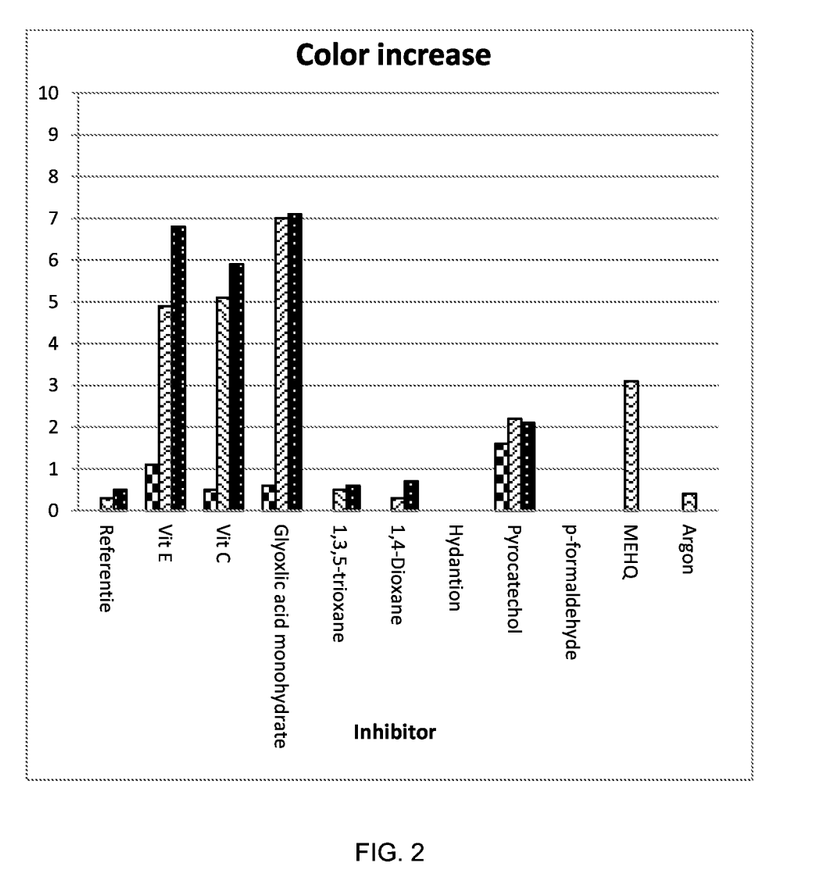
FIG. 2 is a bar graph showing the color increase (increase in color intensity) in the same solutions of a quaternary ammonium hydroxide in a non-aqueous solvent with various candidate inhibitors added as in FIG. 1.

FIG. 2 is a bar graph showing the color increase (increase in color intensity) in the same solutions of DMDPA*OH in propylene glycol with the same candidate inhibitors added as shown in FIG. 1. It is noted that the legend shown in FIG. 1 also applies to FIG. 2, but is not reproduced there for simplicity.

As is clearly evident from Example 1 and FIGS. 1 and 2, hydantoin provides superior inhibition of color formation as compared to other candidate inhibitors and to no inhibitor (Referentie), except for p-formaldehyde and argon. P-formaldehyde is not acceptable due to toxicity and environmental concerns. Argon is not acceptable since once the container has been opened, the argon would be lost and with it, any possible protection from oxidation and color formation and increase.

Example 2

A 20% by weight solution of dimethyldipropylammonium hydroxide (DMDPA*OH) in propylene glycol is prepared. The solution contains water at less than about 0.5% by weight by Karl Fischer titration. Three aliquots of the solution are taken, and 1000 ppm of each of two potential color inhibitor additives are added to one of each of the two aliquots, and nothing is added to the third aliquot ("Referentie"). Each of the three aliquots is divided in half, the first half of each aliquot is held at room temperature for 18 hours, and the second half of each aliquot is held at 50° C. for a total of 308 hours. The Gardner color is determined for each aliquot at zero time, at 18 hours, and for the 50° C. samples, also at 36 hours, 140 hours and 308 hours. The results are shown in FIG. 3 and FIG. 4.

Figure 3:
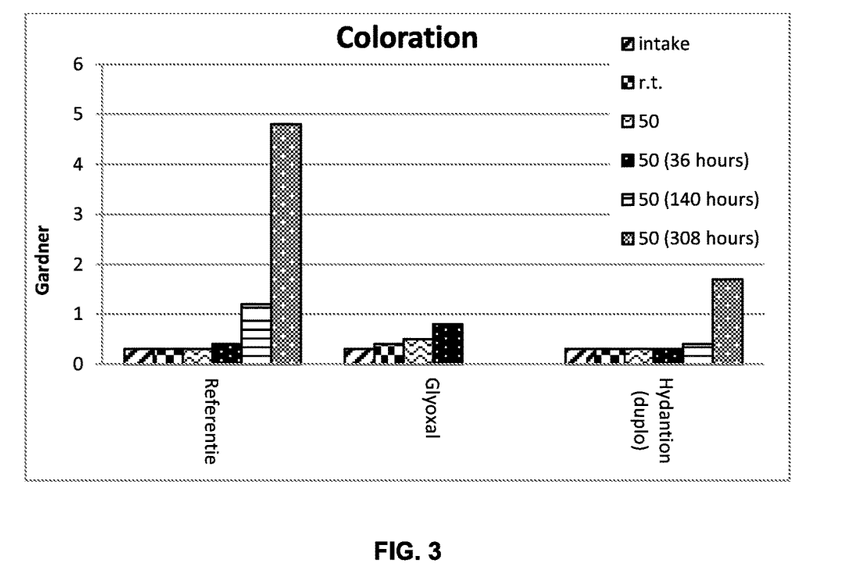
FIG. 3 is a bar graph showing the coloration (color change) in solutions of a quaternary ammonium hydroxide in a non-aqueous solvent with glyoxal and hydantoin added as inhibitors and no inhibitor.

FIG. 3 is a bar graph showing the coloration (color change) in solutions of a quaternary ammonium hydroxide in a non-aqueous solvent with glyoxal and hydantoin added as inhibitors and no inhibitor.

Figure 4:
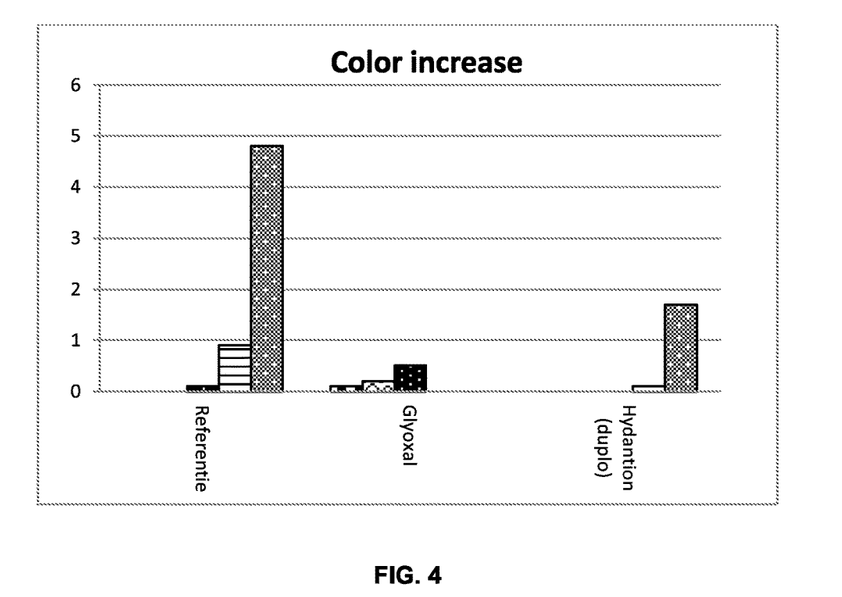
FIG. 4 is a bar graph showing the color increase (increase in color intensity) in the same solutions of a quaternary ammonium hydroxide in a non-aqueous solvent with the same inhibitors as in FIG. 3.

FIG. 4 is a bar graph showing the color increase (increase in color intensity) in the same solutions of a quaternary ammonium hydroxide in a non-aqueous solvent with the same inhibitors as in FIG. 3. It is noted that the legend shown in FIG. 3 also applies to FIG. 4, but is not reproduced there for simplicity.

As is clearly evident from Example 2 and FIGS. 3 and 4, hydantoin provides superior inhibition of color formation as compared to glyoxal and to no inhibitor (Referentie) at all temperatures.

Example 3

A 20% by weight solution of tetramethylammonium hydroxide (TMA*OH) in propylene glycol is prepared. The solution contains water at less than about 0.5% by weight by Karl Fischer titration. Six aliquots of the solution are taken, and 1000 ppm of each of five potential color inhibitor additives are added to one of each of the five aliquots, and nothing is added to the sixth aliquot ("Referentie"). Each of the six aliquots is divided in half, the first half of each aliquot is held at room temperature for 18 hours, and the second half of each aliquot is held at 50° C. for a total of 165 hours. The Gardner color is determined for each aliquot at zero time, at 18 hours, and for the 50° C. samples, also at 90 hours, 140 hours and 165 hours. The results are shown in FIG. 5.

Figure 5:
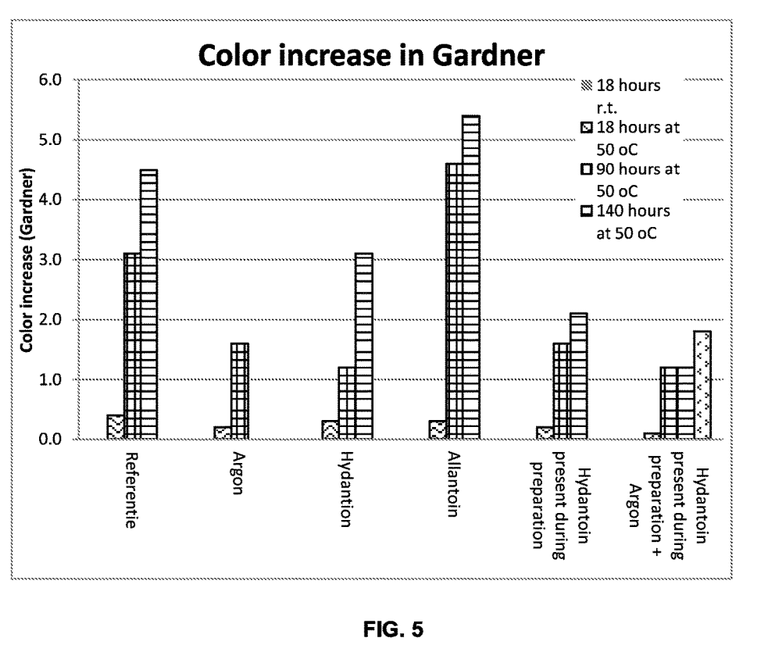
FIG. 5 is a bar graph showing the color increase in solutions of a quaternary ammonium hydroxide in a non-aqueous solvent with various additives as inhibitors as compared to argon and no inhibitor.

FIG. 5 is a bar graph showing the color increase in solutions of a quaternary ammonium hydroxide in a non-aqueous solvent with various additives as inhibitors as compared to argon and no inhibitor.

As is clearly evident from Example 3 and FIG. 5, hydantoin provides superior inhibition of color formation as compared to another candidate inhibitor (allantoin) and to no inhibitor (Referentie). As is evident in FIG. 5, while argon is possibly useful, it does not prevent color increase as well as hydantoin in any form, and argon is not acceptable since once the container has been opened, the argon would be lost and with it, any possible protection from oxidation and color formation and increase. As is further evident from Example 3 and FIG. 5, when hydantoin is present during preparation of the quaternary ammonium hydroxide in a non-aqueous solvent and when hydantoin is present during preparation of the quaternary ammonium hydroxide in a non-aqueous solvent and argon is combined, further improved protection against color increase is observed, as compared to hydantoin added to the previously prepared quaternary ammonium hydroxide in a non-aqueous solvent, particularly at longer exposure times to the increased temperature.

Example 4

A 20% by weight solution of tetramethylammonium hydroxide (TMA*OH) in propylene glycol is prepared. Five aliquots of the solution are taken, and 1000 ppm of hydantoin is added to two of the aliquots (B-1000 and C-1000), 2000 ppm of hydantoin is added to two of the aliquots (B-2000 and C-2000), and no hydantoin is added to one aliquot (A). The TMA*OH solution initially contains water at less than about 0.5% by weight by Karl Fischer titration. To one each of the A, B-1000 and B-2000 aliquots is added sufficient water to increase the Karl Fischer water content to 0.1%. Each of the five aliquots is held at 50° C. for a total of 168 hours. The Gardner color is determined for each aliquot at 24 hours, 48 hours, 72 hours, 96 hours, 120 hours, 144 hours and 168 hours. The results are shown in FIGS. 6 and 7.

Figure 6:
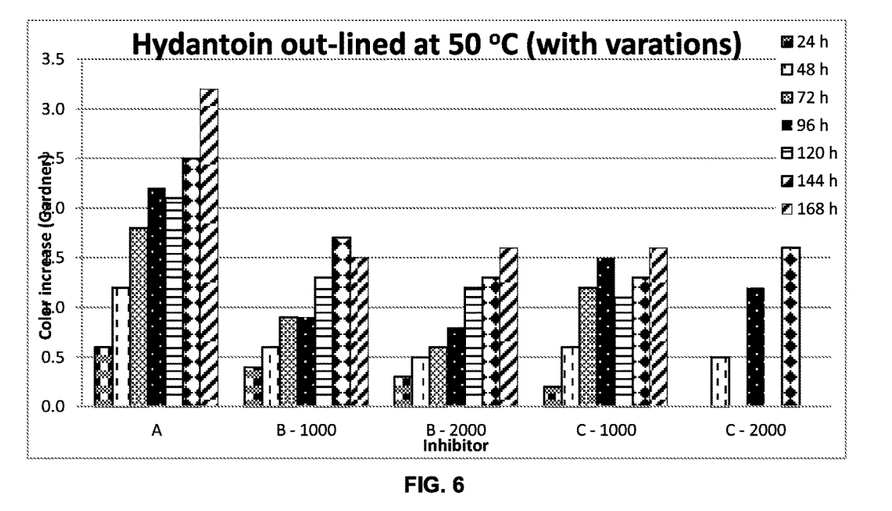
FIG. 6 is a bar graph showing the color increase in solutions of tetramethylammonium hydroxide in propylene glycol with various water contents and hydantoin inhibitor concentrations, as color inhibitor at various times when held at 50° C. for various times.

FIG. 6 is a bar graph showing the color increase in solutions of tetramethylammonium hydroxide in propylene glycol with various water contents and hydantoin inhibitor concentrations, as color inhibitor at various times when held at 50° C. for various times.

Figure 7:
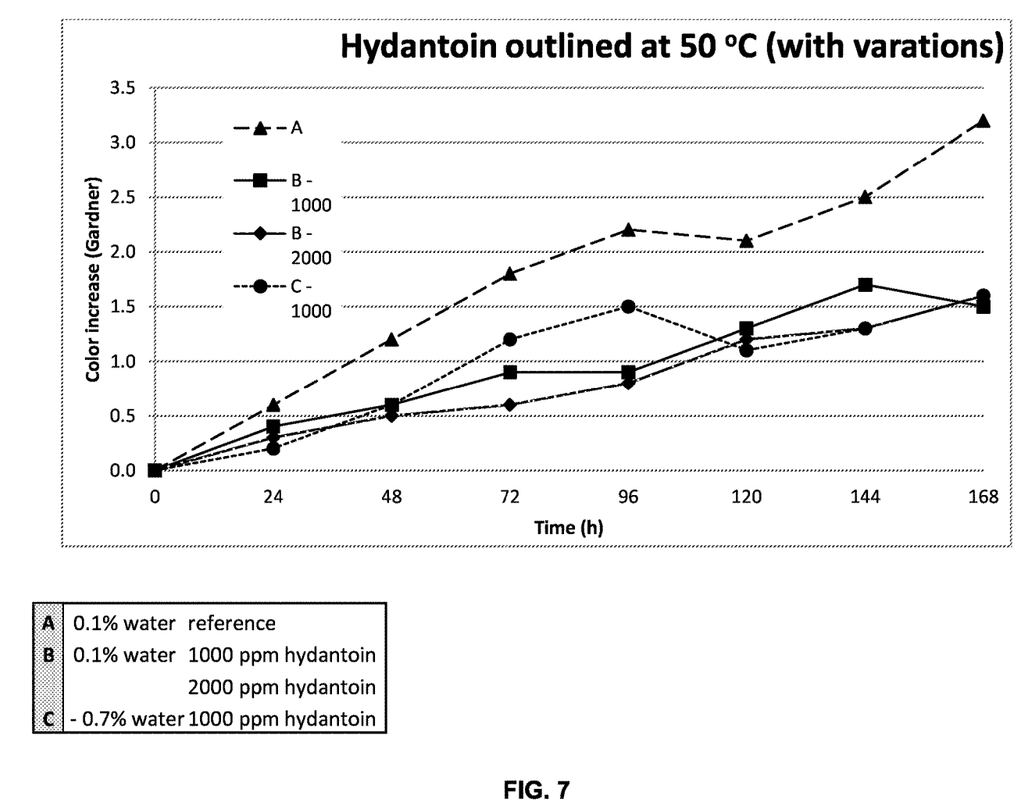
FIG. 7 is a line graph showing the color increase in a solution of tetramethylammonium hydroxide in propylene glycol as described above for Example 4 and similar to the results shown in FIG. 6, when held at 50° C. for a range of times.

FIG. 7 is a line graph showing the color increase in a solution of tetramethylammonium hydroxide in propylene glycol as described above for Example 4 and similar to the results shown in FIG. 6, when held at 50° C. for a range of times. Not all of the samples shown in the FIG. 6 bar graph are included in the FIG. 7 line graph.

As is evident from FIGS. 6 and 7, compared to the reference sample A, the addition of hydantoin at both 1000 ppm and 2000 ppm significantly reduces the color increase in samples of TMA*OH, and 2000 ppm hydantoin may be better than 1000 ppm, and the presence of a small amount of water appears to avoid color increase to some extent.

It is noted that, throughout the specification and claims, the numerical limits of the disclosed ranges and ratios may be combined, and are deemed to include all intervening values. Furthermore, all numerical values are deemed to be preceded by the modifier "about", whether or not this term is specifically stated.

While the principles of the invention have been explained in relation to certain particular embodiments, and are provided for purposes of illustration, it is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the claims.

The invention claimed is:

1. A composition comprising:
   a quaternary onium hydroxide in a non-aqueous solvent, wherein the quaternary onium hydroxide has a concentration in the range from about 20% by weight to about 50% by weight of the composition;
   imidazolidine-2,4-dione, wherein the imidazolidine-2,4-dione has a concentration in the range from about 10 to about 5000 parts per million of the composition, and
   a water content of less than 0.5% by weight of the composition by Karl Fischer titration.

2. The composition of claim 1 wherein the quaternary onium hydroxide comprises an onium ion having a general formula (II):

(II)

wherein in formula (II), A is a nitrogen or phosphorus atom, $R^1$, $R^2$, $R^3$ and $R^4$ are each independently a branched or unbranched alkyl group containing from 1 to about 20 carbon atoms, a branched or unbranched hydroxyalkyl or an alkoxyalkyl group containing from 1 to about 20 carbon atoms, substituted or unsubstituted aryl groups or hydroxyaryl groups containing from 6 to 18 ring carbon atoms, when substituted, said substitution comprises one or more substituent selected from any of the foregoing alkyl, hydroxyalkyl or alkoxyalkyl groups, or $R^1$ and $R^2$ or $R^3$ together with A may form a heterocyclic group provided that if the heterocyclic group contains a C=A group, $R^3$ is the second bond.

3. The composition of claim 2 wherein the quaternary onium hydroxide in formula (II) is a quaternary ammonium hydroxide.

4. The composition of claim 2 wherein at least one of the alkyl groups in formula (II) contains 3 or more carbon atoms.

5. The composition of claim 1 wherein the non-aqueous solvent comprises one or more selected from propylene glycol (PG), butylene glycol (BG), ethylene glycol (EG), triethylene glycol (TEG), formamide (FA), and glycerol (GLY).

* * * * *